Figure 2:
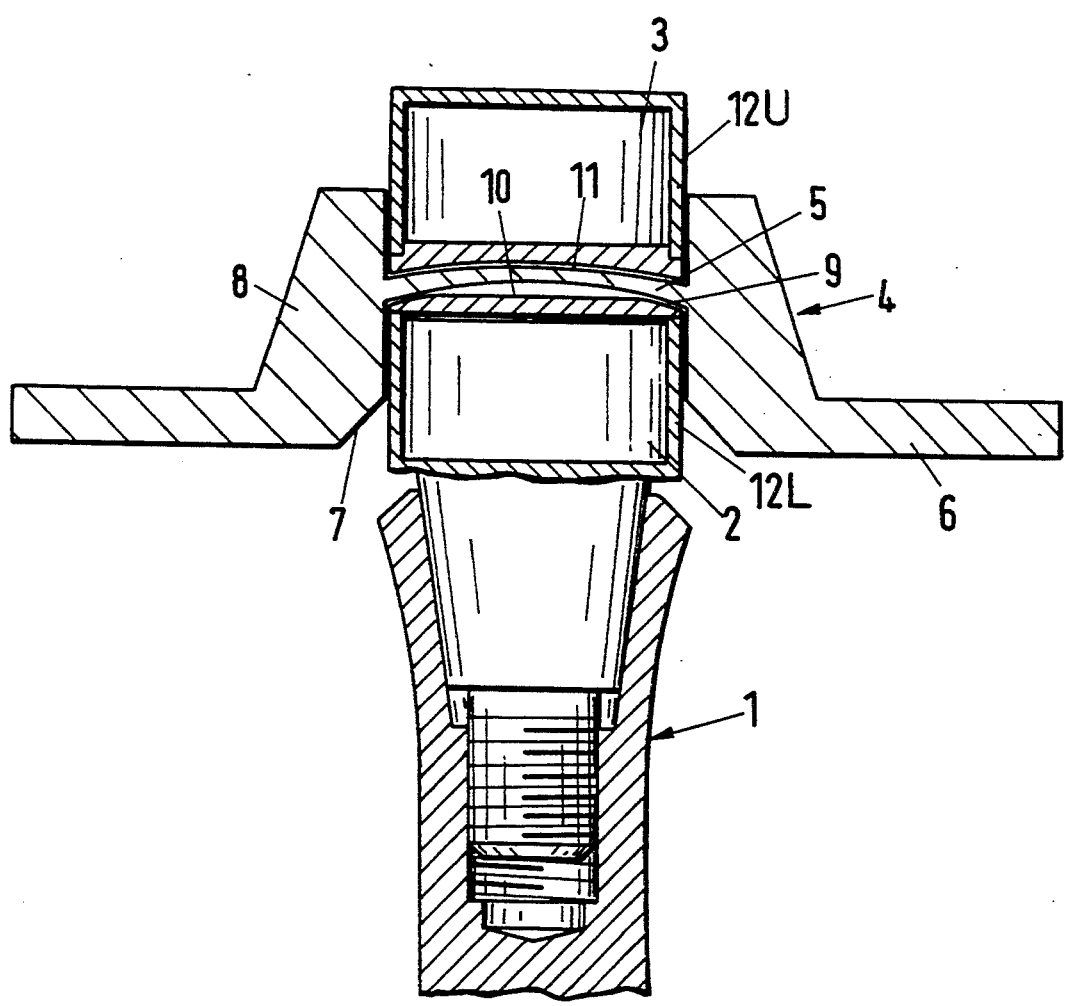

United States Patent
Stemmann

[11] Patent Number: 5,421,722
[45] Date of Patent: Jun. 6, 1995

[54] MAGNET ARRANGEMENT FOR A PROSTHESIS

[76] Inventor: Hartmut Stemmann, Kollaustr. 6, 2000, Hamburg, 54, Germany

[21] Appl. No.: 75,290
[22] Filed: Jun. 11, 1993

[30] Foreign Application Priority Data

Jun. 12, 1992 [DE] Germany .................. 9207951 U

[51] Int. Cl.⁶ .................. A61C 13/235; H01F 7/02
[52] U.S. Cl. .................. 433/189; 433/172; 335/302; 335/306
[58] Field of Search ............ 433/167, 173, 189, 172; 335/302, 306, 303; 403/DIG. 1; 24/303

[56] References Cited

U.S. PATENT DOCUMENTS

| | | | |
|---|---|---|---|
| Re. 34,466 | 12/1993 | Taylor et al. | 128/657 |
| 4,184,252 | 1/1980 | Krol et al. | 433/172 |
| 4,251,791 | 2/1981 | Yanagisawa et al. | 335/302 |
| 4,482,034 | 11/1984 | Baermann | 335/306 X |
| 4,508,507 | 4/1985 | Jackson | 433/189 |
| 4,626,213 | 12/1986 | Shiner et al. | 433/189 X |
| 4,815,975 | 3/1989 | Garrel et al. | |
| 4,993,950 | 2/1991 | Mensor, Jr. | 433/189 X |
| 5,113,872 | 5/1992 | Jahrmarkt et al. | 128/772 |
| 5,123,843 | 6/1992 | Van der Zel et al. | 433/189 |
| 5,191,888 | 3/1993 | Palmer et al. | 128/657 |
| 5,271,415 | 12/1993 | Foerster et al. | 128/772 |

FOREIGN PATENT DOCUMENTS

| | | |
|---|---|---|
| 9347510A1 | 6/1988 | European Pat. Off. |
| 3439955A1 | 5/1986 | Germany |
| 8803488 | 7/1988 | Germany |

Primary Examiner—Nicholas D. Lucchesi
Attorney, Agent, or Firm—Burns, Doane, Swecker & Mathis

[57] ABSTRACT

A magnet arrangement is provided having mutually opposing, cylindrical magnets for securing a prosthesis, one magnet being implanted or fastened to an implant and the opposing magnet being fitted in a prosthesis, in particular a dental prosthesis, wherein the bearing surface of the one magnet is of convex configuration and the bearing surface of the opposing magnet is of concave configuration corresponding to the radius of curvature of the convex bearing surface of the other magnet.

8 Claims, 2 Drawing Sheets

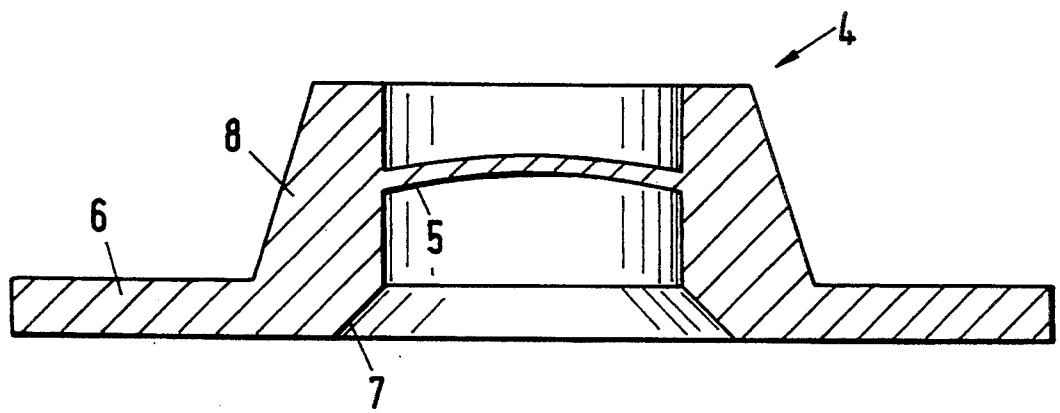
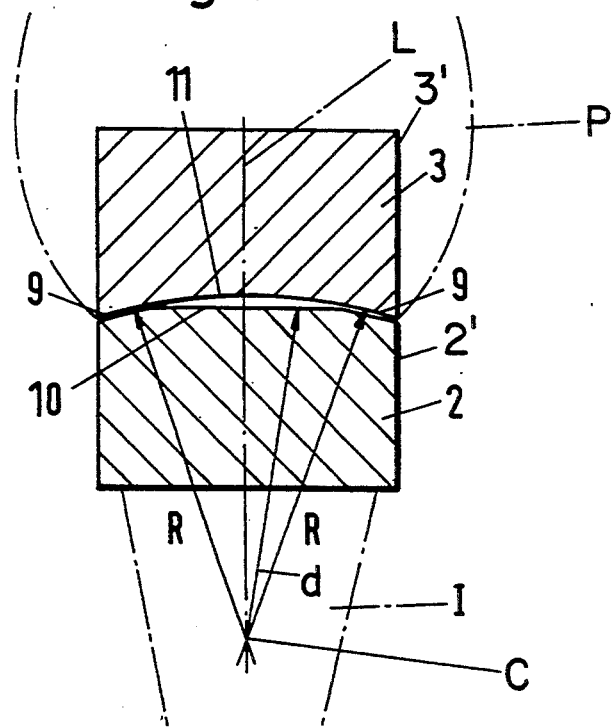

MAGNET ARRANGEMENT FOR A PROSTHESIS

The invention relates to a magnet arrangement for securing a prosthesis, in particular a dental prosthesis, one magnet to be implanted or fastened to an implant and the opposing magnet to be disposed in a prosthesis.

In order, in a magnet arrangement of this type, to obtain a self-centering action when the magnet fastened in the prosthesis is displaced relative to the implanted magnet, for example in chewing motions, the surface of the one magnet is of convex configuration and that of the opposing magnet is, correspondingly, of concave configuration. When, in chewing motions, the prosthesis becomes somewhat displaced in relation to the implanted magnet, a corresponding displacement of the magnet disposed in the prosthesis takes place, whereupon the latter is automatically returned by the magnetic force into the aligned position once the forces acting upon the prosthesis cease.

Furthermore, by virtue of the present invention, a device for positioning a magnet in a prosthesis is proposed, by means of which a magnet to be fitted in a dental prosthesis can be positioned in exact and accurate alignment with an already implanted magnet.

Advantageous designs of the inventions are defined in the following description and in the claims.

By way of example, embodiments of the invention are explained in greater detail below with reference to the drawing, in which:

FIG. 1 shows, in a longitudinal section, two mutually adjoining cylindrical magnets, FIG. 2 shows, in section, the two magnets in conjunction with the positioning device, and FIG. 3 shows the positioning device in section.

FIG. 1 shows, in longitudinal section, a cylindrical magnet 2, which is implanted or fastened to an implant, I and an opposing cylindrical magnet 3, which is fastened in a prosthesis P. The magnet 2 includes a cylindrical side wall 2' and a front bearing surface 9, 10 disposed at one end of the side wall 2'. The magnet 3 includes a cylindrical side wall 3' and a bearing surface 11 disposed at one end of the side wall 3'. The front face 10, lying perpendicular to the longitudinal axis of the cylindrical magnet 2, is rounded in the marginal region 9, such that a convex spherical ring surface 9 is produced having a radius R starting from the axis of the cylindrical magnet.

The opposing front face 11 of the magnet 3 is of continuously concave configuration of the same spherical radius R, so that the two mutually adjoining magnets 2 and 3 bear upon each other only in the marginal region 9, whereas, in the central region of the flat front face 10, there is a clearance between the opposing surfaces. That is, in FIG. 1 the distance d is shorter than radius R. The radii R have a common origin C lying on a longitudinal axis L defined by the cylindrical walls 2', 3'. In this way, a pressure point in the centre of the magnet when supporting the prosthesis is avoided and a self-centring action of the magnets 2 and 3, bearing one upon the other, is produced when the magnet 3 disposed in the prosthesis is deflected in relation to the implanted magnet 2 by displacement motions of the prosthesis.

Instead of being provided with a flattened face 10, the bearing surface of the magnet 2 could comprise a continuous convex spherical surface (not shown), but this results, upon a deflection motion of the magnet 3, in the latter being raised more considerably from the magnet 2 when, for example, the magnet 3 is displaced transversely-to the axis of the arrangement. As a result of the flattening at 10, the magnet 3 is not so considerably raised when it is moved transversely to the axis.

FIG. 2 shows a magnet arrangement having magnets 2 and 3 respectively welded in casings 12L, 12U the concave surface 11 and the spherical ring surface 9 being configured on the opposing surfaces of the respective casing 12L, 12U. At 1, the head part of a dental implant is indicated schematically, in which implant there is inserted the cylindrical magnet 2 with the casing 12L. In order to make it easier to position the magnet 3 accurately in a dental prosthesis, a sleeve-shaped element 4 is provided, this being made from a soft silicone which is licensed in the medical field. The sleeve-shaped element 4 having the sleeve body 8 has, in the lower section, an internal diameter corresponding to the external diameter of the implanted assembly 2, 12L, thereby enabling the sleeve body 8 to be mounted. On the inner periphery, the sleeve body 8 is provided with a partition 5 of predetermined thickness, which partition, on the one hand, limits the depth of immersion of the implanted assembly 2, 12L in the sleeve body 8 and, on the other hand, acts as a spacer for the assembly 3, 12U inserted in the sleeve body 8 from above. The upper section of the sleeve body 8 therefore has an internal diameter corresponding to the external diameter of the assembly 3, 12U. The partition 5 produces a defined air gap between the magnets, which air gap equalises the different resilience of the jaw mucosa when stressed by the dental prosthesis as a result of chewing motions.

The sleeve body 8 has, in the upper region, a wall thickness of approximately 1 mm, which increases in the downward direction to approximately 2 mm, thereby giving rise to a frustoconical outer periphery of the sleeve body 8. Extending radially outwards from the lower edge of the sleeve body 8 is a cover flange 6, which can have, for example, an external diameter of approximately 16 mm. This flange 6 serves to cover the mucosa and can be adapted by the dentist, by cutting to size, according to the respective jaw proportions. For the easier mounting of the element 4 onto the implanted assembly 2, 12L, the lower opening of the sleeve body 8 is bevelled at 7.

When fitting the magnet holder, the lower assembly 2, 12L is first screwed into the implant 1, whereupon the soft silicone element 4 is mounted onto the assembly 2, 12L. The flange 6 covers the mucosa and the thicker, lower section of the sleeve body 8 tightly encloses the magnet assembly 2, 12L. The partition 5 bears primarily upon the spherical ring surface 9. For this purpose, the partition 5 is formed onto the sleeve body in a somewhat upwardly arched configuration, as shown by FIG. 3. The upper magnet 3 is then pressed in as far as the stop on the partition 5. The distance between the upper edge of the sleeve body 8 and the partition 5 is designed such that the magnet assembly 3, 12U protrudes from the sleeve body 8 by a pre-specified amount, for example, 1.5 mm. With this exposed retention surface, the upper magnet assembly 3, 12U is inserted into the prefabricated recess of the dental prosthesis (not represented in FIG. 2). The magnet assembly 3, 12U is thereupon incorporated by polymerisation into the prosthesis by means of liquid autopolymerisate. The sleeve body 8 with cover flange 6 and partition 5 prevents the liquid autopolymerisate from wetting the magnet assembly 2, 12L and the implant.

Once the polymerisate has hardened, the element 4 is removed. As a result of the conical shape of the sleeve body 8, a predetermined cavity is formed between the base of the dental prosthesis and the top part of the implant or the magnet assembly 2, 12L, which cavity extends into the oral cavity, so that, in the event of a displacement motion of the prosthesis transversely to the longitudinal axis, the prosthesis base cannot be supported on the magnet assembly 2, 12L. Any damage to the prosthesis is thereby prevented and undesirable, horizontal thrust forces which would have a harmful effect upon the implant are not transmitted from the prosthesis to the implant anchored firmly in the bone.

The full height of the element 4 in the represented illustrative embodiment can amount, for example, to 3.7 mm. The internal diameter measures 4.4 mm. The partition 5 can be designed having a different thickness to enable the air gap between the magnets to be adapted to different resiliences of the oral mucosa. An embodiment is also possible in which the partition 5 is dispensed with, for example in the case of a terminal dental crown. In this case, the two magnets could bear directly upon each other, as shown by FIG. 1, being centred relative to each other by the sleeve body 8.

In place of the partition 5, radially inwardly projecting lugs can also be formed, as spacers, onto the sleeve body 8. Preferably, a closed partition 5 is provided in order to prevent the penetration of liquid polymerisate.

The element 4 can not only be used for centring the magnet arrangement according to FIG. 1, but also for other magnet pairings in which the two magnets lie opposite each other across a flat end face running perpendicular to the longitudinal axis.

I claim:

1. A magnet arrangement adapted to secure a prosthesis to an implant, said magnet arrangement comprising first and second magnets, one of said magnets adapted to be joined to a prosthesis, and the other of said magnets adapted to be joined to an implant, said first magnet including a cylindrical first side wall and a first bearing surface disposed at one end of said first side wall, said first bearing surface intersected by a longitudinal axis of said first side wall, said second magnet including a cylindrical second side wall and a second bearing surface disposed at one end of said second side wall, said first bearing surface opposing said second bearing surface, said first and second opposing bearing surfaces magnetically coupled together, said first bearing surface being of continuous spherical concave configuration defined by a first radius of curvature, said second bearing surface including an outer marginal region surrounding a central region, said outer marginal region being of spherical convex configuration defined by a second radius of curvature corresponding to said first radius of curvature, said central region being of different configuration than said outer region such that a distance from an origin of said second radius of curvature to said central region is smaller than said second radius of curvature to form a clearance between said first bearing surface and said central region, said central region defining a substantial portion of said second bearing surface, said first and second radii having a common origin lying on said axis.

2. A magnet arrangement according to claim 1, wherein said central region is flat and oriented substantially perpendicular to a longitudinal axis of said second magnet.

3. A magnet arrangement according to claim 1, wherein said first bearing surface is of spherical concave configuration, and said outer marginal region is of spherical convex curvature.

4. A magnet arrangement according to claim 1, wherein said central region constitutes at least one half of the area of said second bearing surface.

5. In combination, a dental prosthesis, a dental implant, and a magnet arrangement securing said dental prosthesis to said dental implant, said magnet arrangement comprising first and second magnets, one of said magnets joined to said dental prosthesis, and the other of said magnets joined to said dental implant, said first magnet including a cylindrical first side wall and a first bearing surface disposed at one end of said first side wall, said first bearing surface intersected by a longitudinal axis of said first side wall, said second magnet including a cylindrical second side wall and a second bearing surface disposed at one end of said second side wall, said first bearing surface opposing said second bearing surface, said first and second opposing bearing surfaces magnetically coupled together, said first bearing surface being of continuous concave configuration defined by a first radius of curvature, said second bearing surface including an outer marginal region surrounding a central region, said outer marginal region being of convex configuration defined by a second radius of curvature corresponding to said first radius of curvature, said central region being of different configuration than said outer region such that a distance from an origin of said second radius of curvature to said central region is smaller than said second radius of curvature, to form a clearance between said first bearing surface and said central region, said central region defining a substantial portion of said second bearing surface.

6. A combination according to claim 5, wherein said first bearing surface is of spherical concave configuration, and said outer marginal region is of spherical convex curvature.

7. A combination according to claim 5, wherein said central region constitutes at least one half of the area of said second bearing surface.

8. In combination, a dental prosthesis, a dental implant, and a magnet arrangement securing said dental prosthesis to said dental implant, said magnet arrangement comprising first and second magnets, one of said magnets joined to said dental prosthesis, and the other of said magnets joined to said dental implant, said first and second magnets forming respective first and second opposing bearing surfaces magnetically coupled together, said first bearing surface being of continuous concave configuration defined by a first radius of curvature, said second bearing surface including an outer marginal region surrounding a central region, said outer marginal region being of convex configuration defined by a second radius of curvature corresponding said first radius of curvature, said central region being of different configuration than said outer region such that a distance from an origin of said second radius of curvature to said central region is smaller than said second radius of curvature, to form a clearance between said first bearing surface and said central region, said central region constituting at least one-half of the area of said second bearing surface.

* * * * *